United States Patent [19]

Lynch et al.

[11] E Patent Number: Re. 33,033

[45] Reissued Date of Patent: Aug. 22, 1989

[54] PROCESS FOR THE PREPARATION OF HMG-COA REDUCTASE INHIBITORS INTERMEDIATES

[75] Inventors: Joseph E. Lynch, Plainfield; Ichiro Shinkai, Westfield; Ralph P. Volante, East Windsor, all of N.J.

[73] Assignee: Merck & Co., Inc., Rahway, N.J.

[21] Appl. No.: 98,171

[22] Filed: Sep. 18, 1987

Related U.S. Patent Documents

Reissue of:

[64] Patent No.: 4,611,081
Issued: Sep. 9, 1986
Appl. No.: 752,323
Filed: Jul. 5, 1985

[51] Int. Cl.[4] ..... C07C 69/74

[52] U.S. Cl. ..... 560/53; 560/60; 560/119; 568/592

[58] Field of Search ..... 560/53, 60, 119; 568/592

[56] References Cited

U.S. PATENT DOCUMENTS

| | | | |
|---|---|---|---|
| 4,137,322 | 1/1979 | Endo et al. | 560/119 |
| 4,346,227 | 8/1982 | Terahara et al. | 560/119 |
| 4,375,475 | 3/1983 | Willard et al. | 549/292 |
| 4,438,277 | 3/1984 | Terahara et al. | 560/119 |
| 4,444,784 | 4/1984 | Hoffman | 560/119 |
| 4,447,626 | 5/1984 | Teroharu et al. | 560/119 |

FOREIGN PATENT DOCUMENTS

| | | | |
|---|---|---|---|
| 2055100 | 2/1981 | United Kingdom | 560/119 |
| 2075013 | 11/1981 | United Kingdom | 560/119 |
| 2077264 | 12/1981 | United Kingdom | 560/119 |

OTHER PUBLICATIONS

J. E. Lynch, *Tetrahedron Letters*, 28, No. 13, 1385, (1987).

M. Braun, *Angew. Chem. Int. Ed., Engl.*, 26, 24, (1987).

*Primary Examiner*—Paul J. Killos

*Attorney, Agent, or Firm*—Melvin Winokur; Joseph F. DiPrima

[57] ABSTRACT

A novel process for intermediates in the synthesis [and] *of* hypercholesterolemic compounds of the HMG-CoA reductase type of the following general formula (1):

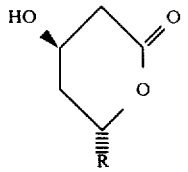

(1)

involving an enantioselective aldol condensation is disclosed.

6 Claims, No Drawings

PROCESS FOR THE PREPARATION OF HMG-COA REDUCTASE INHIBITORS INTERMEDIATES

Matter enclosed in heavy brackets [ ] appears in the original patent but forms no part of this reissue specification; matter printed in italics indicates the additions made by reissue.

BACKGROUND OF THE INVENTION

Hypercholesterolemia is known to be one of the prime etiological components of cardiovascular disease such as atherosclerosis, and there is still no effective antihypercholesterolemic agent available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semi-synthetic and totally synthetic analogs thereof. These compounds have the following general structural formula:

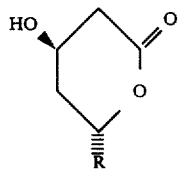

wherein R is

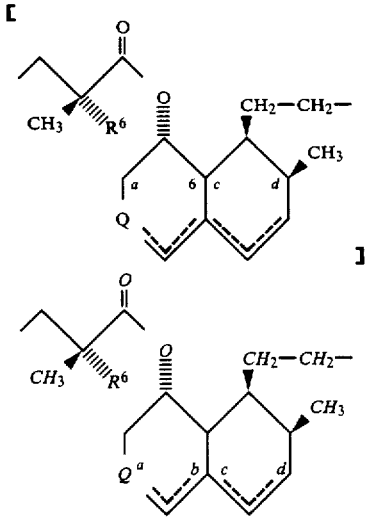

One group of totally synthetic analogs are disclosed in U.S. Pat. No. 4,375,475 and have the same general structural formula:

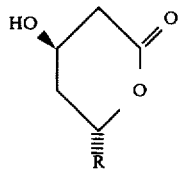

wherein R is

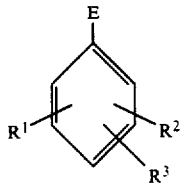

In the usual course of synthesis of these lactones an intermediate ester and dihydroxy acid are encountered:

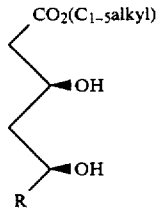

ester

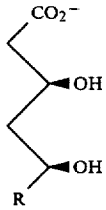

dihydroxy acid

Each of these entities, as well as the lactone, demonstrate antihypercholesterolemic activity in vivo, of comparable magnitude. However, for these compounds to manifest a useful degree of activity, it is essential that the compounds have the particular [3R:5S/3S:5R] steric relationship shown in the structures[.] *above.*

One of the prior art synthesis of these compounds comprises reduction of $\beta$-hydroxyketones 2a or 2b

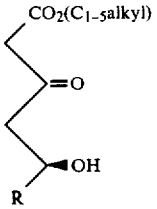

2a or

-continued

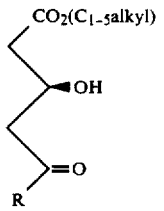

2b

A stereoselective process for the reduction of β-hydroxyketones 2a and 2b [have] *has* been described and disclosed in a copending U.S. patent application Ser. No. 725,891, filed Apr. 25, 1985.

SUMMARY OF THE INVENTION

This invention relates to a novel two step process for the preparation of the intermediate ester 2a in the synthesis of antihypercholesterolemic agents which contain a 4-hydroxy-3,4,5,6-tetrahydro-2H-pyran-2-one moiety. The process involves the enantiomeric aldol condensation of an appropriately substituted aldehyde with the enolate of [(R)-2-acetoxy-1,2,2-triphenylethanol] *(S)-2-acetyloxy-1,1,2-triphenylethanol* and the reaction of the resultant [enolate] *compound* with an alkyl acetate.

DETAILED DESCRIPTION OF THE INVENTION

A process for the preparation of a compound represented by the following general formula (I):

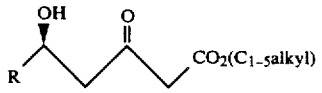

(I)

wherein R is:

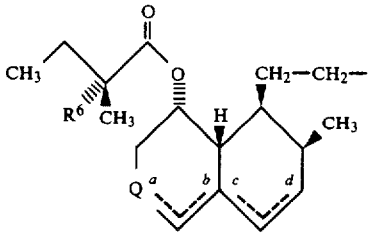

(A)

wherein

Q is

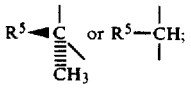

$R^5$ is H or OH;

$R^6$ is hydrogen or methyl; and a,b,c, and d represent optional double bonds, especially where b and d represent double bonds or a,b,c and d are all single bonds; or

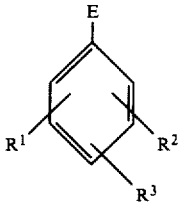

(B)

wherein

E is —CH=CH— or —$CH_2CH_2$—; and $R^1$, $R^2$ and $R^3$ are each selected from halo such as chloro, bromo or fluoro, $C_{1-4}$alkyl, $C_{1-4}$haloalkyl, phenyl phenyl with one or more substituents independently selected from halo $C_{1-4}$alkyl, and $C_{1-4}$alkoxy, or $R^4O$ in which $R^4$ is phenyl, halophenyl, or substituted phenyl-$C_{1-3}$alkyl wherein the substituents are selected from halo and $C_{1-4}$ haloalkyl;

comprises:

(1) reacting a compound of the formula (II)

RCHO (II)

wherein R is defined above, with the enolate of [(R)-2-acetoxy-1,2,2-triphenylethanol] *(S)-2-acetyloxy-1,1,2-triphenylethanol* of the formula (III)

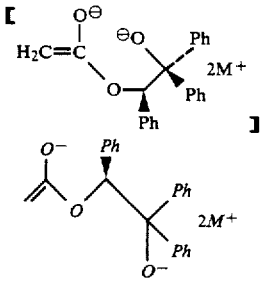

(III)

wherein $M^+$ is a cation derived from sodium, potassium, lithium, magnesium or zinc, to afford a compound of the formula (IV)

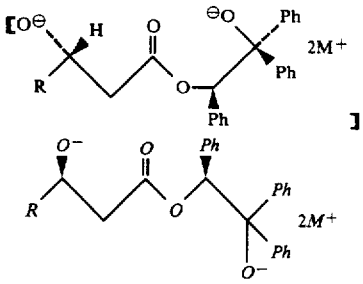

(IV)

wherein R and $M^+$ defined above; and (2) reacting the compound of the formula (IV) with the enolate of a $C_{1-5}$alkylacetate, followed by mild acid hydrolysis to obtain the compounds of the formula (I).

In a first preferred embodiment R is the radical (A). Illustrative of this embodiment are the compounds of the formula I wherein $R^5$ is H, $R^6$ is H or $CH_3$ and b and d represent double bonds or a, b, c and d are all single bonds.

In a second preferred embodiment, R is the radical (B). Illustrative of this embodiment are the compounds of the formula I wherein E is —CH=CH—, $R^1$ is in the 6-position and represents phenyl with 1 or 2 substituents independently selected from chloro, fluoro, methyl and methoxy; and $R^2$ and $R^3$ are independently selected from halo and $C_{1-3}$alkyl in the 2- and 4-positions.

In the most preferred embodiment, R is:

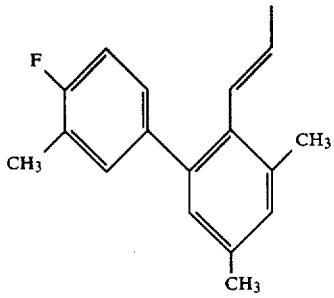

The preparation of the compound of formula (IV) is accomplished by an aldol condensation of the appropriately substituted aldehyde with the enolate of [(R)-2-acetoxy-1,2,2-triphenylethanol] *(S)-2-acetyloxy-1,1,2-triphenylethanol* under standard aldol conditions as described in Braun et al., Tetrahedron Letters, Vol. 25, No. 44, pp 5031-5034 (1984). Specifically the enolate of [(R)-2-alkanoyloxy-1,2,2-triphenylethanol] *(S)-2-alkanoyl-1,1,2-triphenylethanol* is formed under anhydrous conditions in an aprotic solvent utilizing a non-nucleophilic base. Then the appropriately substituted aldehyde is added at low temperatures, between −100° C. and −30° C., preferrably −78° C. and the reaction allowed to go to completion.

The preparation of the compound of the formula (I) is accomplished by a condensation of the compound of the formula (IV), with or without isolation, and with an enolate of a $C_{1-5}$alkyl acetate. When the compound of (IV) is isolated from the reaction mixture of the previous step, it is treated with between 2.0 and 3.0 equivalents, preferrably 2.5 equivalents, of a non-nucleophilic base, in an aprotic solvent, followed by the addition of the enolate of $C_{1-5}$alkyl acetate which is formed in an aprotic solvent with a non-nucleophilic base. When the compound of (IV) is not isolated the enolate of $C_{1-5}$alkyl acetate is added directly to the reaction mixture of the previous step. This condensation is conducted at a temperature between 0° C. and −50° C., preferably −10° for a period of 30 minutes to 16 hours.

Illustrative of the non-nucleophilic bases which may be employed in both steps of this process are alkali metal amides of the formula:

$$[M^{30}N-R^7R^8]\ M^+N^-R^7R^8$$

wherein $M^+$ is a cation derived from sodium, potassium, lithium, magnesium or zinc and $R^7$ and $R^8$ independently are $C_{1-3}$alkyl or when taken together with the nitrogen atom to which they are attached form a 5 or 6-membered heterocyclic ring and alkyl metals such as butyllithium. The preferred non-nucleophilic base is lithium diisopropylamide. Examples of the aprotic solvents that may be employed in both steps of this process are ethers, such as diethyl ether, tetrahydrofuran, 1,2-dimethoxyethane and the like. The preferred solvent is tetrahydrofuran.

The reactions may conveniently be worked up by quenching with saturated ammonium chloride solution, and extracting into an organic solvent.

The starting materials wherein R is the radical (A) may be prepared by using the synthetic methods described by HSU et al., J. Am. Chem. Soc., 1983, 105, pp. 593-601. The starting materials wherein R is the radical (B) are known in the art.

The following examples illustrate the present invention and as such are not to be considered as limiting the invention set forth in the claims appended hereto.

EXAMPLE 1

Preparation of
[(R)-2-[(E)-4-[4'-fluoro-3,3',5-trimethyl[1,'1-bipehnyl]-2-yl]-3-hydroxy-4-pentenoxy]1,2,2-triphenyl ethanol]
*(S)-2-hydroxy-1,2,2-triphenylethyl (E)-5-(4'fluoro-3,3',5-trimethyl[1,1'-biphenyl]-2-yl)-3-hydroxy-4-pentenoate*

[To a suspension of (R)-2-acetoxy-1,2,2-triphenylethanol (332 mg, 1 mmol), prepared according to Braun et al.,] *To a suspension of (S)-2-acetyloxy-1,1,2-triphenylethanol (332 mg, 1 mmol), prepared according to the general procedure of Braun but substituting (S)-mandelic acid in place of (R)-mandelic acid,* in tetrahydrofuran (2 ml) at −78° C. under nitrogen was added lithium diisopropylamide (prepared from 2.2 mmol of butyllithium and 2.42 mmol of diisopropylamine) in tetrahydrofuran (1 ml) and the reaction mixture [was] allowed to warm to 0° C. To the reaction mixture which was recooled to −78° C. was added E-3-(4'-fluoro-3,3',5-trimethyl[1,1'-biphenyl]-2-yl)-propenal in tetrahydrofuran (1 ml) [was added]. After 30 minutes at −78° C. the reaction was quenched with a saturated solution of ammonium chloride. The desired product was extracted into ethyl acetate, dried over magnesium sulfate, and flash chromatographed over silica gel with hexane:ethylacetate(4:1) to give a yellow wax.

EXAMPLE 2

Preparation of tert-butyl
(E)-7-(4'-fluoro-3,3',5-trimethyl-[1,1-biphenyl]-2-yl)-3-oxo-5-hydroxy-6-heptenoate Lithium diisopropylamide (6.65 mmol) was prepared by the addition of 4.75 ml of 1.4M n-butyllithium in hexanes to a solution of diisopropylamine (665 mg, 6.65 mmol) in 10 ml of tetrahydrofuran at −25° C. to −35° C. The mixture was stirred for 30 minutes at −25° C. and cooled to −78° C. t-Butylacetate (771 mg, 6.65 mmol) was added dropwise and the solution was stirred for 30 minutes at −78° C. and then warmed to −25° C. over 1 hour. A solution of [(R)-2-[(E)-4-(4'-fluoro-3,3',5-trimethyl]1,1'-biphenyl]-2-yl]-3-hydroxy-4-pentenoxy)-1,2,2-triphenylethanol] *(S)-2-hydroxy-1,2,2-triphenylethyl(E)-5-(4'-fluoro-3,3',5-trimethyl-[1,1'-biphenyl[-2yl)-3-hydroxy-4-pentenoate* (800 mg, 1.33 mmol) in 2 ml tetrahydrofuran was added and the mixture was stirred for 1 hour at −25° C. and warmed to 22°-24° C. and stirred for 16 hours. The reaction mixture was quenched with a saturated solution of ammonium chloride and the product was extracted into methylene chloride, dried over sodium sulfate and concentrated in vacuo to give the titled product.

EXAMPLE 3

Preparation of tert-butyl (E)-7-(4'-fluoro-3,3',5-trimethyl-[1,1'-biphenyl]-2-yl)-3-oxo-5-hydroxy-6-heptenoate (one-pot)

To a suspension of [(R)2-acetoxy-1,1,2-triphenylethanol] *(S)=2-acetoxy-1,1,2-triphenylethanol* (166 mg, 0.5 mmol) in tetrahydrofuran (1 ml) at −78° C. under nitrogen was added lithium diisopropylamide (prepared from 1.2 mmol butyllithium and 1.2 mmol of diisopropylamine) in tetrahydrofuran (0.5 ml) and the reaction was allowed to warm to 0° C. To the reaction mixture which was recooled to −78° C. was added E-3-(4'-fluoro-3,3',5-trimethyl-[1,1'-biphenyl]-2-yl)-propenal (132 mg, 0.5 mmol) in tetrahydrofuran (0.5 ml). After 30 minutes at −78° C., to the reaction mixture lithium tert butylacetate (prepared from tert butyl acetate 3.0 mmol, butyllithium 3.0 mmol and diisopropylamine 3.0 mmol) in tetrahydrofuran (3.0 ml) was added and the reaction mixture allowed to warm to −20° C. over 30 minutes. The mixture was then warmed to 22° and stirred *for* 16 hours. The reaction was quenched with a saturated solution of ammonium chloride and the product extracted into methylene chloride. The organic phase was washed with saturated sodium chloride, dried over sodium sulfate and concentrated in vacuo to afford the above titled product.

EXAMPLES 4 TO 13

Utilizing the general procedures of Examples 1 and 2 or 3, the following compounds of the Formula I are prepared from the appropriate starting materials.

| Compound Number | [R¹] R |
|---|---|
| 4 | 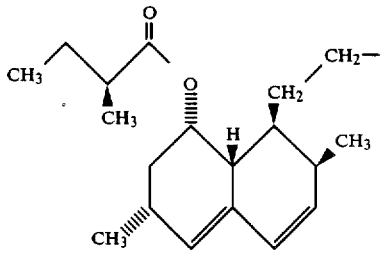 |
| 5 | 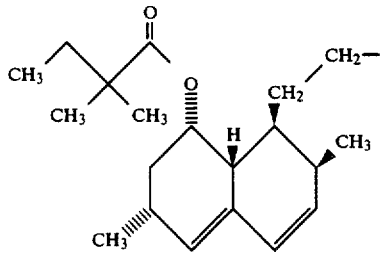 |
| 6 | 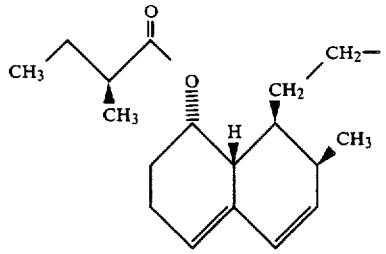 |

-continued

| Compound Number | [R¹]ep R |
|---|---|
| 7 | 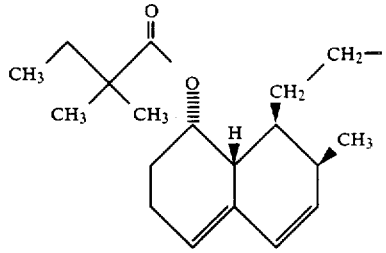 |
| 8 | 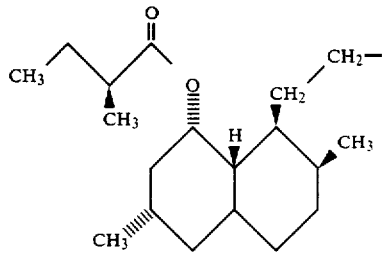 |
| 9 | 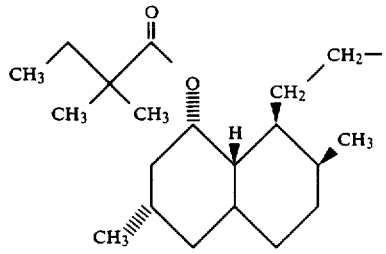 |
| 10 | 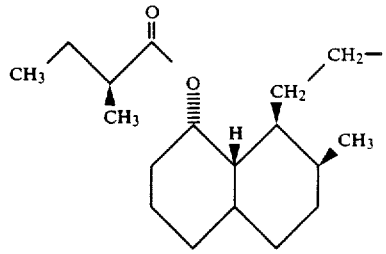 |
| 11 | 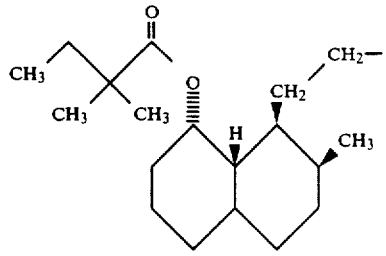 |
| 12 | 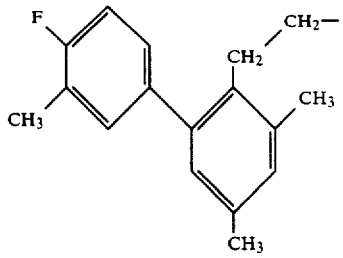 |

-continued

| Compound Number | [R¹] R |
|---|---|
| 13 | 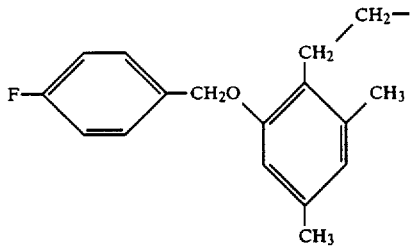 |

What is claimed is:

1. A process for the preparation of a compound represented by the following general formula (I):

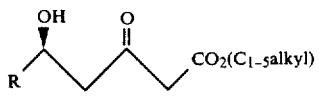

(I)

wherein

R is:

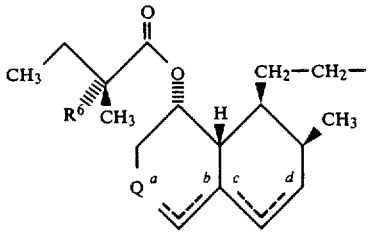

(A)

wherein

Q is

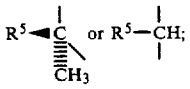

$R^5$ is H or OH;

$R^6$ is hydrogen or methyl; and a, b, c, and d represent optional double bonds, especially where b and d represent double bonds or a, b, c and d are all single bonds; or

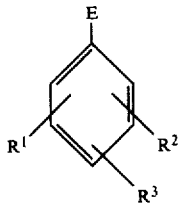

(B)

wherein

E is —C=CH— or —$CH_2CH_2$—; and $R^1$, $R^2$ and $R^3$ are each selected from halo such as chloro, bromo or fluoro, $C_{1-4}$alkyl, $C_{1-4}$haloalkyl, phenyl phenyl with one or more substituents independently selected from halo, $C_{1-4}$alkyl, and $C_{1-4}$alkoxy, or $R^4O$ in which $R^4$ is phenyl, halophenyl, or substituted phenyl-$C_{1-3}$alkyl wherein the substituents are selected from halo and $C_{1-4}$haloalkyl;

which comprises:

(1) reacting a compound of the formula (II)

RCHO (II)

wherein R is defined above, with the enolate of [(R)-2-acetoxy-1,2,2-triphenylethanol] *(S)-2-acetyloxy-1,1,2-triphenylethanol* of the formula (III)

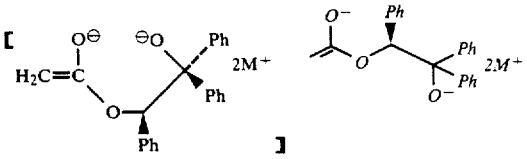

(III)

wherein M+ is a cation derived from sodium, potassium, lithium, magnesium, or zinc, to afford a compound of the formula (IV)

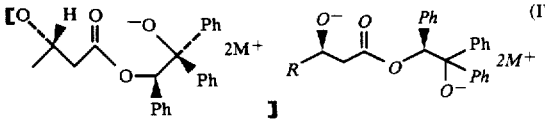

(IV)

wherein R and M+ are defined above; and (2) reacting the compound of the formula (IV) with the enolate of a $C_{1-5}$alkylacetate, followed by mild acid hydrolysis to obtain the compounds of the formula (I).

2. A process according to claim 1 wherein the compound of the formula (III) is prepared by treating [(R)-2-acetoxy-1,2,2-triphenylethanol] *(S)-1-acetyloxy-1,1,2-triphenylethanol* with a non-nucleophilic base [employed to form the enolate of the compound of the formula (III) is an alkali metal amide of the formula:] *of formula:*

$M^+N^-R^7R^8$ wherein M+ is a cation derived from sodium, potassium lithium, magnesium or zinc and $R^7$ and $R^8$ independently are $C_{1-3}$alkyl or when taken together with the nitrogen to which they are attached form a 5 or 6-membered heterocyclic ring.

3. A process according to claim 1 wherein the compound of the Formula (IV) is not isolated and the reactions are conducted in an aprotic solvent.

4. A process according to claim 1 wherein R is the radical (B).

5. A process according to claim 4 wherein E is —CH=CH—, $R^1$ is in the 6-position and represents a phenyl with 1 or 2 substituents independently selected from chloro, fluoro, methyl and methoxy and $R^2$ and $R^3$ are independently selected from halo and $C_{1-3}$alkyl in the 2- and 4-position.

6. A process according to claim 5 for the preparation of $C_{1-5}$alkyl (E)-7-(4'-fluoro-3,3',5-trimethyl-[1,1'-biphenyl]-2-yl)-3-oxo-5-hydroxy-6-heptenoate.

* * * * *